United States Patent
Chevalier et al.

(10) Patent No.: US 10,246,532 B2
(45) Date of Patent: Apr. 2, 2019

(54) CATALYST COMPONENTS FOR THE POLYMERIZATION OF OLEFINS

(71) Applicant: BASELL POLIOLEFINE ITALIA S.R.L., Milan (IT)

(72) Inventors: Reynald Chevalier, Compiegne (FR); Alessandro Mignogna, Ferrara (IT); Giampiero Morini, Ferrara (IT)

(73) Assignee: Basell Poliolefine Italia S.r.l., Milan (IT)

( * ) Notice: Subject to any disclaimer, the term of this patent is extended or adjusted under 35 U.S.C. 154(b) by 0 days.

(21) Appl. No.: 15/557,704

(22) PCT Filed: Mar. 8, 2016

(86) PCT No.: PCT/EP2016/054903
§ 371 (c)(1),
(2) Date: Sep. 12, 2017

(87) PCT Pub. No.: WO2016/142377
PCT Pub. Date: Sep. 15, 2016

(65) Prior Publication Data
US 2018/0051106 A1    Feb. 22, 2018

(30) Foreign Application Priority Data
Mar. 12, 2015 (EP) .................................. 15158824

(51) Int. Cl.
*C08F 110/06* (2006.01)
*C07F 7/28* (2006.01)

(52) U.S. Cl.
CPC .............. *C08F 110/06* (2013.01); *C07F 7/28* (2013.01)

(58) Field of Classification Search
None
See application file for complete search history.

(56) References Cited

U.S. PATENT DOCUMENTS

| | | |
|---|---|---|
| 6,303,715 B1 | 10/2001 | Kim et al. |
| 2012/0157642 A1 | 6/2012 | Chen et al. |
| 2013/0131293 A1 | 5/2013 | Mignogna et al. |
| 2014/0011670 A1 | 1/2014 | Chen et al. |

FOREIGN PATENT DOCUMENTS

DE     19927979 A1    10/2000

*Primary Examiner* — Catherine S Branch

(57) ABSTRACT

A solid catalyst component which exhibits high activity and stereospecificity in the polymerization of olefins made from or containing Mg, Ti and an electron donor of formula (I)

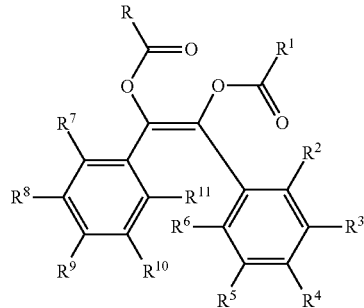

where R and $R^1$ are selected from the group consisting of $C_1$-$C_{20}$ hydrocarbon groups, $C_6$-$C_{14}$ aryl or alkylaryl groups hydrocarbon groups, optionally containing a heteroatom selected from the group consisting of halogens, P, S, N, and O; $R^2$ to $R^{11}$ groups, equal to or different from each other, are hydrogen, halogen or $C_1$-$C_{15}$ hydrocarbon groups which can be optionally fused together to form one or more cycles with the proviso that $R^6$ and $R^{11}$ cannot join together to form a phenyl ring.

12 Claims, No Drawings

CATALYST COMPONENTS FOR THE POLYMERIZATION OF OLEFINS

This application is the U.S. National Phase of PCT International Application PCT/EP2016/054903, filed Mar. 8, 2016, claiming benefit of priority to European Patent Application No. 15158824.1, filed Mar. 12, 2015, the contents of which are incorporated herein by reference in its entirety.

FIELD OF THE INVENTION

In general, the present disclosure relates to the field of chemistry. More specifically, the present disclosure relates to polymer chemistry. In particular, the present disclosure relates to catalyst components for the polymerization of olefins made from or containing a Mg dihalide based support on which are supported Ti atoms and an electron donor compound containing a diolester derivative. The present disclosure further relates to the catalysts obtained from the components and to their use in processes for the polymerization of olefins.

BACKGROUND OF THE INVENTION

Concerning the polymerization of propylene, Ziegler-Natta catalysts can be made from or contain a solid catalyst component, constituted by a magnesium dihalide on which are supported a titanium compound and an internal electron donor compound, used in combination with an Al-alkyl compound. When higher crystallinity of the polymer is desired, an external donor can be used to obtain higher isotacticity. Internal donors can be constituted by the esters of phthalic acid. The phthalates can be used as internal donors in combination with alkylalkoxysilanes as external donors. This catalyst system gives good performances in terms of activity, isotacticity and xylene insolubility.

The use of this catalyst system has raised health concerns.

SUMMARY OF THE INVENTION

In a general embodiment, the present disclosure provides a catalyst component for the polymerization of olefins made from or containing Mg, Ti, halogen and an electron donor of formula (I)

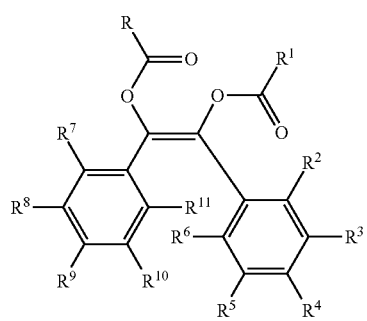

(I)

where R and $R^1$ are selected from $C_1$-$C_{20}$ hydrocarbon groups, $C_6$-$C_{14}$ aryl or alkylaryl groups hydrocarbon groups, optionally containing a heteroatom selected from halogen, P, S, N, O;
$R^2$ to $R^{11}$ groups, equal to or different from each other, are hydrogen, halogen or $C_1$-$C_{15}$ hydrocarbon groups which can be optionally fused together to form one or more cycles with the proviso that $R^6$ and $R^{11}$ cannot join together to form a phenyl ring.

DETAILED DESCRIPTION OF THE INVENTION

In some embodiments, structures of formula (I) are those in which R and $R^1$ groups are phenyl groups. In some embodiments, the phenyl groups bear at least one substituent selected from $C_1$-$C_{15}$ hydrocarbon groups or halogen. In some embodiments, the hydrocarbon groups substituents are $C_1$-$C_{10}$ alkyl groups, $C_6$-$C_{14}$ aryl groups, $C_3$-$C_{15}$ cycloalkyl groups, and $C_7$-$C_{15}$ arylalkyl or alkylaryl groups. In other embodiments, the hydrocarbon groups are $C_1$-$C_{10}$ alkyl groups, alternatively, linear $C_1$-$C_5$ alkyl groups. In other embodiments, the hydrocarbon substituents are located in 4-position.

In some embodiments, halogens are substituents. In other embodiments, the halogens are selected from the group consisting of Cl, Br and F. In some embodiments, the halogens are Cl. In some embodiments, the substituents' positions are meta, para, or both. In some embodiments, other positions in addition to meta and/or para are substituted with halogens and/or hydrocarbon groups.

In some embodiments, all of the $R^2$ to $R^{11}$ groups are hydrogen. In some embodiments, one or more of the $R^2$ to $R^{11}$ groups are selected from $C_1$-$C_{15}$ hydrocarbon groups which can be optionally fused together to form one or more cycles.

In some embodiment, the final amount of electron donor compound in the solid catalyst component ranges from about 1 to about 25% by weight, based upon the total weight of the solid catalyst component, alternatively in the range from about 3 to about 20% by weight.

In some embodiments, the structures of formulas (I) are the following: 1,2-diphenylethene-1,2-diyl bis(2,2-dimethylpropanoate), 1,2-diphenylethene-1,2-diyl bis(4-butylbenzoate), 1,2-diphenylethene-1,2-diyl bis(4-chlorobenzoate), 1,2-diphenylethene-1,2-diyl bis(4-ethylbenzoate), 1,2-diphenylethene-1,2-diyl bis(4-methylbenzoate), 1,2-diphenylethene-1,2-diyl bis(4-propylbenzoate), 1,2-diphenylethene-1,2-diyl bis(furan-2-carboxylate), 1,2-diphenylethene-1,2-diyl bis(thiophene-2-carboxylate), 1,2-diphenylethene-1,2-diyl diacetate, 1,2-diphenylethene-1,2-diyl dibenzoate, 1,2-di-p-tolylethene-1,2-diyl bis(2,2-dimethylpropanoate), 1,2-di-p-tolylethene-1,2-diyl bis(4-butylbenzoate), 1,2-di-p-tolylethene-1,2-diyl bis(4-chlorobenzoate), 1,2-di-p-tolylethene-1,2-diyl bis(4-ethylbenzoate), 1,2-di-p-tolylethene-1,2-diyl bis(4-methylbenzoate), 1,2-di-p-tolylethene-1,2-diyl bis(4-propylbenzoate), 1,2-di-p-tolylethene-1,2-diyl bis(furan-2-carboxylate), 1,2-di-p-tolylethene-1,2-diyl bis(thiophene-2-carboxylate), 1,2-di-p-tolylethene-1,2-diyl diacetate, 1,2-di-p-tolylethene-1,2-diyl dibenzoate, 1,2-bis(4-chlorophenyl)ethene-1,2-diyl bis(2,2-dimethylpropanoate), 1,2-bis(4-chlorophenyl)ethene-1,2-diyl bis(4-butylbenzoate), 1,2-bis(4-chlorophenyl)ethene-1,2-diyl bis(4-chlorobenzoate), 1,2-bis(4-chlorophenyl)ethene-1,2-diyl bis(4-ethylbenzoate), 1,2-bis(4-chlorophenyl)ethene-1,2-diyl bis(4-methylbenzoate), 1,2-bis(4-chlorophenyl)ethene-1,2-diyl bis(4-propylbenzoate), 1,2-bis(4-chlorophenyl)ethene-1,2-diyl bis(furan-2-carboxylate), 1,2-bis(4-chlorophenyl)ethene-1,2-diyl bis(thiophene-2-carboxylate), 1,2-bis(4-chlorophenyl)ethene-1,2-diyl diacetate, 1,2-bis(4-chlorophenyl)ethene-1,2-diyl dibenzoate, 1,2-di-o-tolylethene-1,2-diyl bis(2,2-dimethylpropanoate), 1,2-di-o-tolylethene-1,2-diyl bis(4-butylbenzoate), 1,2-di-o-tolylethene-1,2-diyl bis(4-chlorobenzoate), 1,2-di-o-tolylethene-1,2-diyl bis(4-ethylbenzoate), 1,2-di-o-tolylethene-1,2-diyl bis(4-methylbenzoate), 1,2-di-o-tolylethene-1,2-diyl bis(4-propylbenzoate), 1,2-di-o-tolylethene-1,2-diyl bis(furan-2-carboxylate), 1,2-di-o-tolylethene-1,2-diyl bis(thiophene-2-carboxylate), 1,2-di-o-tolylethene-1,2-diyl diacetate, 1,2-di-o-tolylethene-1,2-diyl dibenzoate, 1,2-bis(2-chlorophenyl)ethene-1,2-diyl bis(2,2-dimethylpropanoate), 1,2-bis(2-chlorophenyl)ethene-1,2-diyl bis(4-butylbenzoate), 1,2-bis(2-chlorophenyl)ethene-1,2-diyl bis(4-chlorobenzoate), 1,2-bis(2-chlorophenyl)ethene-1,2-diyl bis(4-ethylbenzoate), 1,2-bis(2-chlorophenyl)ethene-1,2-diyl bis(4-methylbenzoate), 1,2-bis(2-chlorophenyl)ethene-1,2-diyl bis(4-propylbenzoate), 1,2-bis(2-chlorophenyl)ethene-1,2-diyl bis(furan-2-carboxylate), 1,2-bis(2-chlorophenyl)ethene-1,2-diyl bis(thiophene-2-carboxylate), 1,2-bis(2-chlorophenyl)ethene-1,2-diyl diacetate, 1,2-bis(2-chlorophenyl)ethene-1,2-diyl dibenzoate, 1,2-bis(2,6-dimethylphenyl)ethene-1,2-diyl bis(2,2-dimethylpropanoate), 1,2-bis(2,6-dimethylphenyl)ethene-1,2-diyl bis(4-butylbenzoate), 1,2-bis(2,6-dimethylphenyl)ethene-1,2-diyl bis(4-chlorobenzoate), 1,2-bis(2,6-dimethylphenyl)ethene-1,2-diyl bis(4-ethylbenzoate), 1,2-bis(2,6-dimethylphenyl)ethene-1,2-diyl bis(4-methylbenzoate), 1,2-bis(2,6-dimethylphenyl)ethene-1,2-diyl bis(4-propylbenzoate), 1,2-bis(2,6-dimethylphenyl)ethene-1,2-diyl bis(furan-2-carboxylate), 1,2-bis(2,6-dimethylphenyl)ethene-1,2-diyl bis(thiophene-2-carboxylate), 1,2-bis(2,6-dimethylphenyl)ethene-1,2-diyl diacetate, 1,2-bis(2,6-dimethylphenyl)ethene-1,2-diyl dibenzoate, 1,2-dimesitylethene-1,2-diyl bis(2,2-dimethylpropanoate), 1,2-dimesitylethene-1,2-diyl bis(4-butylbenzoate), 1,2-dimesitylethene-1,2-diyl bis(4-chlorobenzoate), 1,2-dimesitylethene-1,2-diyl bis(4-ethylbenzoate), 1,2-dimesitylethene-1,2-diyl bis(4-methylbenzoate), 1,2-dimesitylethene-1,2-diyl bis(4-propylbenzoate), 1,2-dimesitylethene-1,2-diyl bis(furan-2-carboxylate), 1,2-dimesitylethene-1,2-diyl bis(thiophene-2-carboxylate), 1,2-dimesitylethene-1,2-diyl diacetate, 1,2-dimesitylethene-1,2-diyl dibenzoate, 1,2-bis(4-fluorophenyl)ethene-1,2-diyl dibenzoate, 1,2-di(naphthalen-1-yl)ethene-1,2-diyl dibenzoate, 1,2-di(naphthalen-2-yl)ethene-1,2-diyl dibenzoate, 1,2-diphenylethene-1,2-diyl bis(1-naphthoate), 1,2-diphenylethene-1,2-diyl bis(2-naphthoate), 1-(2,6-dimethylphenyl)-2-phenylethene-1,2-diyl dibenzoate, 1-(2-chlorophenyl)-2-phenyl ethene-1,2-diyl dibenzoate, 1-mesityl-2-phenyl ethene-1,2-diyl dibenzoate, 1-phenyl-2-(o-tolyl)ethene-1,2-diyl dibenzoate, 1-phenyl-2-(p-tolyl)ethene-1,2-diyl dibenzoate, 1,2-bis(4-(tert-butyl)phenyl)ethene-1,2-diyl bis(2,2-dimethylpropanoate), 1,2-bis(4-(tert-butyl)phenypethene-1,2-diyl bis(4-butylbenzoate), 1,2-bis(4-(tert-butyl)phenyl)ethene-1,2-diyl bis(4-chlorobenzoate), 1,2-bis(4-(tert-butyl)phenyl)ethene-1,2-diyl bis(4-ethylbenzoate), 1,2-bis(4-(tert-butyl)phenyl)ethene-1,2-diyl bis(4-methylbenzoate), 1,2-bis(4-(tert-butyl)phenyl)ethene-1,2-diyl bis(4-propylbenzoate), 1,2-bis(4-(tert-butyl)phenyl)ethene-1,2-diyl bis(furan-2-carboxylate), 1,2-bis(4-(tert-butyl)phenyl)ethene-1,2-diyl bis(thiophene-2-carboxylate), 1,2-bis(4-(tert-butyl)phenyl)ethene-1,2-diyl diacetate, 1,2-bis(4-(tert-butyl)phenyl)ethene-1,2-diyl dibenzoate.

In some embodiments, the compounds falling in formula (I) can be prepared by reacting 1,2-diarylketone with metallic magnesium then with an acyl chloride.

In some embodiments, the amount of Ti atoms in the solid catalyst component is higher than about 2.5% wt alternatively, higher than about 3.0%, with respect to the total weight of the solid catalyst component.

In some embodiments, the catalyst components are made from or contain, in addition to the electron donors, Ti, Mg and halogen. In some embodiments, the catalyst components are made from or contain a titanium compound, having at least a Ti-halogen bond and the electron donor compounds supported on a Mg halide. In some embodiments, the magnesium halide is $MgCl_2$ in active form.

In some embodiments, the titanium compounds are $TiCl_4$ and $TiCl_3$. In some embodiments, the titanium compounds are Ti-haloalcoholates of formula $Ti(OR)_{m-y}X_y$, where m is the valence of titanium, y is a number between 1 and m-1, X is halogen and R is a hydrocarbon radical having from 1 to 10 carbon atoms.

In some embodiments, the preparation of the solid catalyst component includes a reaction between magnesium alcoholates or chloroalcoholates and an excess of $TiCl_4$ in the presence of the electron donor compounds at a temperature of about 80 to 120° C.

In some embodiments, the solid catalyst component can be prepared by reacting a titanium compound of formula $Ti(OR)_{m-y}X_y$, where m is the valence of titanium and y is a number between 1 and m, alternatively $TiCl_4$, with a magnesium chloride deriving from an adduct of formula $MgCl_2 \cdot pROH$, where p is a number between 0.1 and 6, alternatively from 2 to 3.5, and R is a hydrocarbon radical having 1-18 carbon atoms. In some embodiments, the adduct is prepared in spherical form by mixing alcohol and magnesium chloride in the presence of an inert hydrocarbon immiscible with the adduct, operating under stirring conditions at the melting temperature of the adduct (100-130° C.). Then, the emulsion is quickly quenched, thereby causing the solidification of the adduct in form of spherical particles. In some embodiments, the resulting adduct is directly reacted with Ti compound. In some embodiments, the resulting adduct is subjected to thermal controlled dealcoholation (80-130° C.) to obtain an adduct in which the number of moles of alcohol is lower than 3, alternatively between 0.1 and 2.5. In some embodiments, the reaction with the Ti compound is carried out by suspending the adduct in cold $TiCl_4$; the mixture is heated up to 80-130° C. and kept at this temperature for 0.5-2 hours. In some embodiments, the adduct is dealcoholated. The treatment with $TiCl_4$ can be carried out one or more times. In some embodiments, the electron donor compound is added during the treatment with $TiCl_4$. In some embodiments, the preparation of catalyst components in spherical form is described in European Patent Applications Nos. EP-A-395083, EP-A-553805, EP-A-553806, and EPA601525 or Patent Cooperation Treaty Publication No. WO98/44001, incorporated herein by reference.

In some embodiments, the solid catalyst components show a surface area (by B.E.T. method) between about 20 and about 500 m$^2$/g and alternatively between about 50 and about 400 m$^2$/g, and a total porosity (by B.E.T. method) higher than about 0.2 cm$^3$/g, alternatively between about 0.2 and about 0.6 cm$^3$/g. The porosity (Hg method) due to pores with radius up to about 10.000 Å, may ranges from about 0.3 to about 1.5 cm$^3$/g, alternatively from about 0.45 to about 1 cm$^3$/g.

In some embodiments, the solid catalyst component has an average particle size ranging from about 5 to about 120 μm, alternatively from about 10 to about 100 μm.

In some embodiments, the desired electron donor compounds can be added or, alternatively, obtained in situ by using an appropriate precursor capable to be transformed in the electron donor compound. In some embodiments, the in situ process can be achieved chemical reactions.

In some embodiments, the final amount of the electron donor compound of formula (I) is such that its molar ratio with respect to the Ti atoms is from about 0.01 to about 2, alternatively from about 0.05 to about 1.5.

In some embodiments, the solid catalyst components are converted into catalysts for the polymerization of olefins by reacting the solid catalyst components with organoaluminum compounds.

In some embodiments, the present disclosure provides a catalyst for the polymerization of olefins $CH_2=CHR$, in which R is hydrogen or a hydrocarbyl radical with 1-12 carbon atoms, made from or containing a product obtained by contacting:
(i) the solid catalyst component and
(ii) an alkylaluminum compound and optionally,
(iii) an external electron donor compound.

In some embodiments, the alkyl-Al compound (ii) is chosen among trialkyl aluminum compounds, including, for example, triethylaluminum, triisobutylaluminum, tri-n-butylaluminum, tri-n-hexylaluminum, and tri-n-octylaluminum. In some embodiments, the alkyl-Al compound is selected from the group consisting of alkylaluminum halides, alkylaluminum hydrides or alkylaluminum sesquichlorides. In some embodiments, the alkyl-Al compounds is selected from the group consisting of $AlEt_2Cl$ and $Al_2Et_3Cl_3$. In some embodiments, the alkyl-Al compound is a mixture including trialkylaluminums.

In some embodiments, the external electron-donor compounds are selected from the group consisting of silicon compounds, ethers, esters, amines, heterocyclic compounds, and ketones. In some embodiments, the external electron-donor compound is 2,2,6,6-tetramethylpiperidine.

In some embodiments, the external donor compounds are silicon compounds of formula $(R_7)_a(R_8)_bSi(OR_9)_c$, where a and b are integers from 0 to 2, c is an integer from 1 to 4 and the sum (a+b+c) is 4; $R_7$, $R_8$, and $R_9$, are radicals with 1-18 carbon atoms optionally containing heteroatoms. In some embodiments, the silicon compounds have a is 1, b is 1, c is 2, at least one of $R_7$ and $R_8$ is selected from branched alkyl, cycloalkyl or aryl groups with 3-10 carbon atoms optionally containing heteroatoms and $R_9$ is a $C_1$-$C_{10}$ alkyl group. In some embodiments, the $R_9$ is methyl. In some embodiments, the silicon compounds are selected from the group consisting of methylcyclohexyldimethoxysilane (C donor), diphenyldimethoxysilane, methyl-t-butyldimethoxysilane, dicyclopentyldimethoxysilane (D donor), diisopropyldimethoxysilane, (2-ethylpiperidinyl)t-butyldimethoxysilane, (2-ethylpiperidinyl)thexyldimethoxysilane, (3,3,3-trifluoro-n-propyl)(2-ethylpiperidinyl)dimethoxysilane, methyl(3,3,3-trifluoro-n-propyl)dimethoxysilane, and N,N-diethylaminotriethoxysilane. In other embodiments, the silicon compounds have a is 0, c is 3, $R_8$ is a branched alkyl or cycloalkyl group, optionally containing heteroatoms, and $R_9$ is methyl. In some embodiments, the silicon compounds are selected from the group consisting of cyclohexyltrimethoxysilane, t-butyltrimethoxysilane and thexyltrimethoxysilane.

In some embodiments, the electron donor compound (iii) is used in an amount to give a molar ratio between the organoaluminum compound and the electron donor compound (iii) of from about 0.1 to about 500, alternatively from about 1 to about 300 and alternatively from about 3 to about 100.

In some embodiments, the present disclosure provides a process for the polymerization or copolymerization of olefins $CH_2=CHR$, in which R is hydrogen or a hydrocarbyl radical with 1-12 carbon atoms, carried out in the presence of a catalyst made from or containing a product of the reaction between:
(i) the solid catalyst component;
(ii) an alkylaluminum compound and,
(iii) optionally an electron-donor compound (external donor).

In some embodiments, the polymerization process is carried out in slurry polymerization using, as diluent, an inert hydrocarbon solvent, or bulk polymerization using the liquid monomer as a reaction medium. In some embodiments, the liquid monomer is propylene. In some embodiments, the polymerization process occurs in gas-phase operating in one or more fluidized or mechanically agitated bed reactors.

In some embodiments, the polymerization temperature may range from about 20 to about 120° C., alternatively from about 40 to about 80° C. When the polymerization is carried out in gas-phase, the operating pressure can range from about 0.5 to about 5 MPa, alternatively between about 1 and about 4 MPa. In the bulk polymerization, the operating pressure may range from about 1 to about 8 MPa, alternatively between about 1.5 and about 5 MPa.

The following examples are given in order to further illustrate the disclosure without being intended as limiting it.

Characterizations

Determination of X.I.

In a round-bottomed flask provided with a cooler and a reflux condenser, 2.5 g of polymer and 250 ml of o-xylene were placed and kept under nitrogen. The mixture was heated to 135° C. and kept under stirring for about 60 minutes. The final solution was allowed to cool to 25° C. under continuous stirring, and the insoluble polymer was then filtered. The filtrate was then evaporated in a nitrogen flow at 140° C. to reach a constant weight. The content of the xylene-soluble fraction was expressed as a percentage of the original 2.5 grams and then, by difference, the X.I. %.

Determination of Donors.

The content of electron donor was determined by gas-chromatography. The solid component was dissolved in acidic water. The solution was extracted with ethyl acetate, an internal standard was added, and a sample of the organic phase was analyzed in a gas chromatograph, to determine the amount of donor present at the starting catalyst compound.

Melt Flow Rate (MFR)

The melt flow rate MIL of the polymer was determined according to ISO 1133 (230° C., 2.16 Kg).

EXAMPLES

General Procedure for Preparation of the Spherical Adducts

An initial amount of microspheroidal $MgCl_2\cdot 2.8C_2H_5OH$ was prepared according to the method described in Example 2 of Patent Cooperation Treaty Publication No. WO98/44009, incorporated herein by reference but operating on a larger scale.

General Procedure for the Preparation of the Solid Catalyst Component

Into a 500 mL round bottom flask, equipped with mechanical stirrer, cooler and thermometer 250 mL of $TiCl_4$ were introduced at room temperature under nitrogen atmosphere. After cooling to 0° C., while stirring, the internal donor and 10.0 g of the spherical adduct were sequentially added into the flask. The charged internal donor was in an amount sufficient to charge a Mg/donor molar ratio of 6. The temperature was raised to 100° C. and maintained for 2 hours. Thereafter, stirring was stopped, the solid product was allowed to settle and the supernatant liquid was siphoned off at 100° C. After the supernatant was removed, additional fresh $TiCl_4$ was added to reach the initial liquid volume again. The mixture was then heated at 120° C. and kept at this temperature for 1 hour. Stirring was stopped again. The solid was allowed to settle. The supernatant liquid was siphoned off.

The solid was washed with anhydrous hexane six times (6×100 mL) in temperature gradient down to 60° C. and one time (100 mL) at room temperature. The solid was then dried under vacuum and analyzed.

General Procedure for the Polymerization of Propylene

A 4-liter steel autoclave equipped with a stirrer, pressure gauge, thermometer, catalyst feeding system, monomer feeding lines and thermostating jacket, was purged with nitrogen flow at 70° C. for one hour. Then, at 30° C. under propylene flow, the autoclave was charged in sequence with 75 mL of anhydrous hexane, 0.76 g of $AlEt_3$, dicyclopentyldimethoxysilane in an amount sufficient to have a Al/donor molar ratio of 20 and 0.006÷0.010 g of solid catalyst component. The autoclave was closed; subsequently 2.0 NL of hydrogen were added. Then, under stirring, 1.2 kg of liquid propylene was fed. The temperature was raised to 70° C. in five minutes and the polymerization was carried out at this temperature for two hours. At the end of the polymerization, the non-reacted propylene was removed; the polymer was recovered and dried at 70° C. under vacuum for three hours. Then the polymer was weighed and fractionated with o-xylene to determine the amount of the xylene insoluble (X.I.) fraction.

Synthesis of Donor of Example 1

In a 250 mL round bottom flask, under nitrogen, the following components were introduced: THF (50 mL), magnesium turnings (1.16 g, 47.6 mmol) and a catalytic amount of iodine. After 5 minutes, benzil (10 g, 47.6 mmol) dissolved in THF (20 mL) was added dropwise in one hour under stirring and cooling. After two hours of post-reaction time, benzoyl chloride (13.8 mL, 119 mmol) dissolved in THF (40 mL) was added dropwise under stirring and cooling. The mixture was stirred for addition two hours then diluted with water and diethyl ether. The organic layer was separated and washed with water until neutral pH, then anhydrified over $Na_2SO_4$. The solvent was distilled off to afford 1,2-diphenylethene-1,2-diyl dibenzoate.

Synthesis of Donor of Example 2

The procedure was the same as that used in the synthetic example 1 except that 3-chlorobenzoyl chloride was used instead of benzoyl chloride.

Synthesis of Donor of Example 3

The procedure was the same as that used in the synthetic example 1 except that 4-n-propylbenzoyl chloride was used instead of benzoyl chloride.

Examples 1-3

The catalyst components were prepared using the donors indicated in Table 1. The solid catalyst components were analyzed for their composition and tested in polymerization of propylene. The results are listed in Table 1.

TABLE 1

| | Catalyst compostion | | Polymerization | | |
|---|---|---|---|---|---|
| | Internal Donor | Ti | Mileage | XI | MIL |
| | Structure | % wt | % wt | kg/g | % wt | g/10' |
| 1 | (1,2-diphenylethene-1,2-diyl dibenzoate structure) | 5.0 | 4.4 | 37.5 | 97.0 | 2.1 |
| 2 | (bis(3-chlorobenzoate) structure) | nd | 4.3 | 48.7 | 98.0 | 1.1 |
| 3 | (bis(4-n-propylbenzoate) structure) | nd | 4.8 | 58.7 | 96.1 | 2.3 | nd: not determined

What is claimed is:

1. A solid catalyst component for the polymerization of olefins comprising:
   (i) Mg,
   (ii) Ti,
   (iii) halogen, and
   (iv) an electron donor of formula (I)

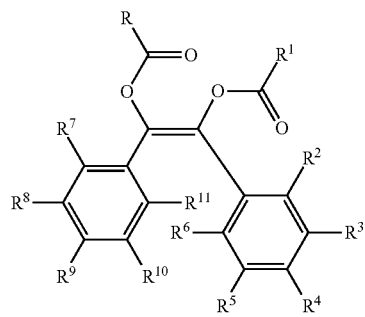

wherein

R and $R^1$ are selected from the group consisting of $C_1$-$C_{20}$ hydrocarbon groups, and $C_6$-$C_{14}$ aryl or alkylaryl groups, wherein R and $R^1$ optionally contain a heteroatom selected from the group consisting of halogen, P, S, N, and O; and $R^2$ to $R^{11}$ groups, equal to or different from each other, are selected from the group consisting of hydrogen, halogen and $C_1$-$C_{15}$ hydrocarbon groups which are optionally fused together to form one or more cycles with the proviso that $R^6$ and $R^{11}$ cannot join together to form a phenyl ring.

2. The catalyst component according to claim 1, wherein R and $R^1$ groups are phenyl groups.

3. The catalyst component according to claim 2, wherein the phenyl groups bear at least one substituent selected from the group consisting of $C_1$-$C_{15}$ hydrocarbon groups and halogens.

4. The catalyst component according to claim 3, wherein the hydrocarbon substituent is selected from the group consisting of $C_1$-$C_{10}$ alkyl groups, $C_6$-$C_{14}$ aryl groups, $C_3$-$C_{15}$ cycloalkyl groups, and $C_7$-$C_{15}$ arylalkyl or alkylaryl groups.

5. The catalyst component according to claim 4, wherein the hydrocarbon substituent is selected the group consisting of linear $C_1$-$C_5$ alkyl groups.

6. The catalyst component according to claim 4, wherein the hydrocarbon substituent is located in 4-position.

7. The catalyst component according to claim 3, wherein the halogen substituent is Cl.

8. The catalyst component according to claim 7, wherein the Cl is located in the meta position, the para position, or both.

9. The catalyst component according to claim 1, wherein the $R^2$ to $R^{11}$ groups are hydrogens.

10. A catalyst for the polymerization of olefins comprising:
    (a) a product of a reaction between:
        (i) a solid catalyst component comprising:
            (A) Mg,
            (B) Ti,
            (C) halogen, and
            (D) an electron donor of formula (I)

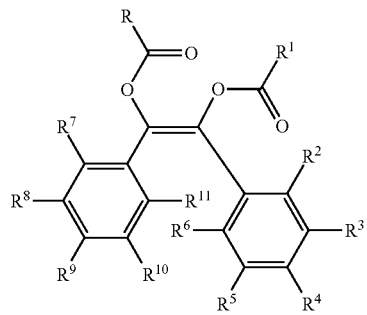

wherein

R and $R^1$ are selected from the group consisting of $C_1$-$C_{20}$ hydrocarbon groups, and $C_6$-$C_{14}$ aryl or alkylaryl groups, wherein R and $R^1$ optionally contain a heteroatom selected from the group consisting of halogen, P, S, N, and O;

$R^2$ to $R^{11}$ groups, equal to or different from each other, are selected from the group consisting of hydrogen, halogen and $C_1$-$C_{15}$ hydrocarbon groups which are optionally fused together to form one or more cycles with the proviso that $R^6$ and $R^{11}$ cannot join together to form a phenyl ring, and (ii) an alkylaluminum compound and optionally, (iii) an external electron donor compound.

11. The catalyst according to claim 10 further comprising an external electron donor compound.

12. A process for polymerization or copolymerization of an olefin comprising:
    (a) polymerizing an olefin $CH_2$=CHR, wherein R is hydrogen or a hydrocarbyl radical with 1-12 carbon atoms in the presence of a catalyst system comprising:
        (A) a product of a reaction between:
            i. a solid catalyst component comprising:
                (1) Mg,
                (2) Ti,
                (3) halogen, and
                (4) an electron donor of formula (I)

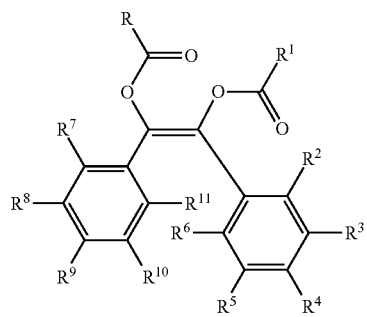

wherein

R and $R^1$ are selected from the group consisting of $C_1$-$C_{20}$ hydrocarbon groups, and $C_6$-$C_{14}$ aryl or alkylaryl groups, wherein R and $R^1$ optionally contain a heteroatom selected from the group consisting of halogen, P, S, N, and O;

$R^2$ to $R^{11}$ groups, equal to or different from each other, are selected from the group consisting of hydrogen, halogen and $C_1$-$C_{15}$ hydrocarbon groups which are optionally fused together to form one or more cycles with the proviso that $R^6$ and $R^{11}$ cannot join together to form a phenyl ring, ii. an alkylaluminum compound, and iii. optionally an external donor compound.

* * * * *